(12) United States Patent
Biedermann

(10) Patent No.: US 12,207,851 B2
(45) Date of Patent: *Jan. 28, 2025

(54) MODULAR BONE PLATE AND MEMBER OF SUCH A MODULAR BONE PLATE

(71) Applicant: Biedermann Technologies GmbH & Co. KG, Donaueschingen (DE)

(72) Inventor: Markku Biedermann, Miami, FL (US)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/138,649

(22) Filed: Apr. 24, 2023

(65) Prior Publication Data

US 2023/0380876 A1 Nov. 30, 2023

Related U.S. Application Data

(63) Continuation of application No. 17/141,497, filed on Jan. 5, 2021, now Pat. No. 11,666,364, which is a
(Continued)

(51) Int. Cl.
*A61B 17/80* (2006.01)
*A61B 17/70* (2006.01)

(52) U.S. Cl.
CPC ...... *A61B 17/8057* (2013.01); *A61B 17/7059* (2013.01); *A61B 17/80* (2013.01);
(Continued)

(58) Field of Classification Search
CPC . A61B 17/80; A61B 17/8023; A61B 17/8042; A61B 17/8061
See application file for complete search history.

(56) References Cited

U.S. PATENT DOCUMENTS 6,645,208 B2 * 11/2003 Apfelbaum ............ A61B 17/80
606/281
7,303,564 B2 * 12/2007 Freid .................... A61B 17/808
606/247

(Continued)

FOREIGN PATENT DOCUMENTS

| CN | 104224291 A | 12/2014 |
| WO | 2012/172517 A1 | 12/2012 |
| WO | 2012/172519 A1 | 12/2012 |

OTHER PUBLICATIONS

EP Search Report dated Nov. 16, 2017 of Application No. EP 17153947.

*Primary Examiner* — Anu Ramana
(74) *Attorney, Agent, or Firm* — Gordon & Jacobson, P.C.

(57) ABSTRACT

A modular bone plate includes a first plate member including a first connection portion having a first hole and a second plate member including a second connection portion having a second hole. The first plate member is connectable to the second plate member when the first plate member and the second plate member are arranged such that the first hole and the second hole overlap. The modular bone plate also includes a connector member that is insertable into the first hole and the second hole when the first hole and the second hole overlap such as to connect the first plate member and the second plate member. The connector member includes a passage that is configured to accommodate a portion of a bone anchor therein.

15 Claims, 9 Drawing Sheets

Related U.S. Application Data continuation of application No. 15/809,267, filed on Nov. 10, 2017, now Pat. No. 10,898,245.

(60) Provisional application No. 62/421,683, filed on Nov. 14, 2016.

(52) U.S. Cl.
CPC ...... *A61B 17/8023* (2013.01); *A61B 17/8042* (2013.01); *A61B 17/8061* (2013.01)

(56) References Cited

U.S. PATENT DOCUMENTS

| | | | |
|---|---|---|---|
| 7,326,212 B2* | 2/2008 | Huebner | A61B 17/8061 606/328 |
| 8,337,534 B2* | 12/2012 | Celli | A61B 17/8042 606/289 |
| 8,834,533 B2* | 9/2014 | Michelson | A61B 17/7059 606/280 |
| 9,028,498 B2 | 5/2015 | Hershgold | |
| 9,486,250 B2* | 11/2016 | Altarac | A61B 17/7059 |
| 9,629,672 B2* | 4/2017 | Angelucci | A61B 17/8023 |
| 9,668,794 B2 | 6/2017 | Kuster | |
| 9,956,016 B2 | 5/2018 | Biedermann | |
| 10,159,515 B2 | 12/2018 | Ehmke et al. | |
| 10,166,054 B2 | 1/2019 | Woodburn | |
| 10,188,437 B2* | 1/2019 | Angelucci | A61B 17/8004 |
| 10,213,237 B2* | 2/2019 | Wiederkehr | A61B 17/8014 |
| 10,517,656 B2 | 12/2019 | Biedermann | |
| 10,898,245 B2 | 1/2021 | Biedermann | |
| 10,980,584 B2 | 4/2021 | Brace | |
| 2002/0183757 A1 | 12/2002 | Michelson | |
| 2004/0074189 A1 | 4/2004 | Deschenes | |
| 2006/0276794 A1 | 12/2006 | Stern | |
| 2007/0276405 A1* | 11/2007 | Huebner | A61B 17/80 606/105 |
| 2009/0082813 A1 | 3/2009 | Long et al. | |
| 2009/0275947 A1* | 11/2009 | Graham | A61B 17/8061 606/280 |
| 2010/0121328 A1 | 5/2010 | Reitzig et al. | |
| 2012/0022600 A1 | 1/2012 | Overes et al. | |
| 2012/0029579 A1 | 2/2012 | Bottlang et al. | |
| 2014/0081269 A1 | 3/2014 | Biedermann | |
| 2014/0100572 A1 | 4/2014 | Biedermann | |
| 2015/0018829 A1 | 1/2015 | Woodburn, Sr. et al. | |
| 2015/0289910 A1 | 10/2015 | Mirghasemi et al. | |
| 2015/0320462 A1 | 11/2015 | Biedermann | |
| 2021/0128209 A1 | 5/2021 | Biedermann | |

* cited by examiner

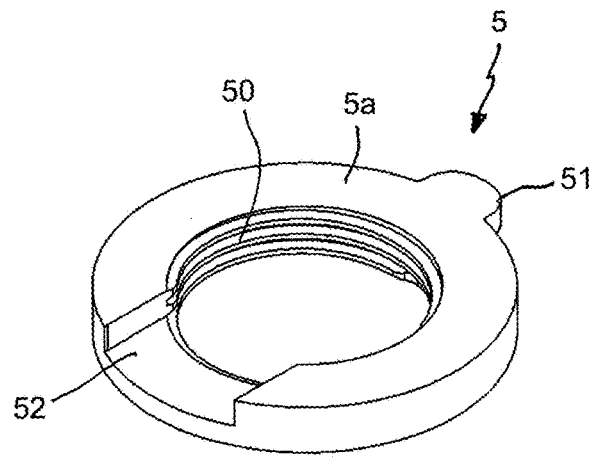
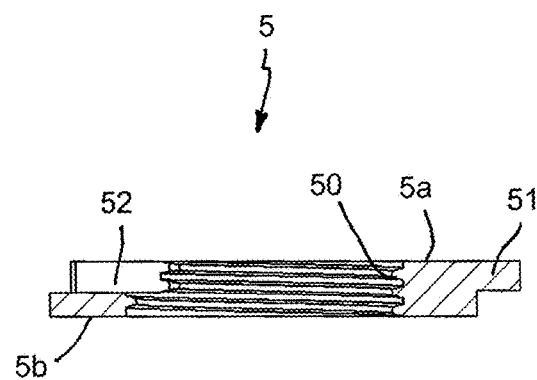
Fig. 19                Fig. 20
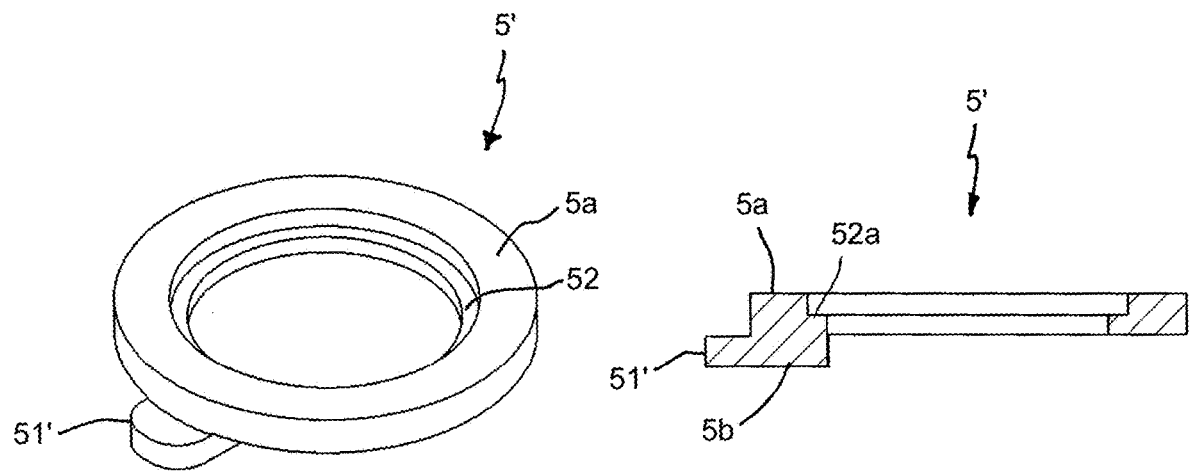
Fig. 21                Fig. 22

MODULAR BONE PLATE AND MEMBER OF SUCH A MODULAR BONE PLATE

CROSS-REFERENCE TO RELATED APPLICATIONS

This application is a continuation of U.S. Ser. No. 17/141,497, filed Jan. 5, 2021, which is a continuation of U.S. Ser. No. 15/809,267, filed Nov. 10, 2017, now issued as U.S. patent Ser. No. 10/898,245, which claims benefit from U.S. Provisional Ser. No. 62/421,683, filed Nov. 14, 2016, all of which are hereby incorporated by reference in their entireties herein.

BACKGROUND

1. Field of the Invention

The invention relates to a modular bone plate and to a member of such a modular bone plate. With such a modular bone plate and the member thereof a plate system for generating various shapes and types of bone plates to be used for osteosynthesis of fragmented bones and for stabilization of bones can be provided.

2. State of the Art

Various shapes and types of bone plates to be used for osteosynthesis of fragmented bones and for stabilization of bones are known. The shape, size and type of a bone plate are usually adapted to the bones that shall be stabilized or immobilized. Hence, a large inventory of bone plates is typically necessary to be able to treat many different kinds of fractures or other defects at different locations.

US 2014/0081269 A1 describes a modular bone plate and a member of such a modular bone plate that permits to generate various shapes and types of bone plates by connecting at least two members of the modular bone plate. The at least two members of the modular bone plate are connected at their respective connection portions such that a projection of the connection portion of a first member is introduced into a groove of a connection portion of a second member. In the assembled configuration, the holes of the connection portions are arranged concentrically on top of each other. Through the holes a bone anchor can be inserted that fixes the bone plate to the bone. Alternatively, a screw can be used to connect the plate members together.

It is the object of the invention to provide a modular bone plate and a member of such a modular bone plate that provides an increased variety of applications.

In an embodiment, the modular bone plate includes a first and a second plate member wherein each plate member has a connection portion with a hole. The connection portions each have a projection and a groove and the bone plate is assembled in that the projection of one plate member is inserted into the groove of the other plate member by laterally shifting the plate members towards each other. A width of the projection may be smaller than a width of the plate member. By means of this design bending forces acting onto the bone plate can be transferred from one plate member to the other plate member. The projections may be formed as lugs projecting from the connection portion. Thereby the stiffness of the bone plate against bending can be increased.

In an embodiment, a connector member is insertable into the holes to connect the plate members together. The connector member may be configured to accommodate a portion of a bone anchor therein in such a manner that the bone anchor can assume various angles with respect to the bone plate when inserted into the connector member. Different connector members each configured to accommodate a different bone anchor may be provided. The bone anchors may differ with respect to their shank diameter and/or head diameter or other features. The connector members differ only with respect to their internal shape such as a seat portion for the bone anchor and/or a size of a passage for guiding through a shank of the bone anchor. The outer shape that cooperates with the connection portions is the same. Hence, the variety of applications of the modular bone plate are increased.

Using the connector members increases the strength of the connection between the plate members. In a further embodiment, instead of a connector member, a plug member may be used for closing the overlapping holes of the connection portions. In a still further embodiment the bone anchors may be secured against backing out by a locking member that cooperates with the connector member.

The plate member may have various shapes and sizes that allow to generate a bone plate adapted to the specific conditions of use. Due to the modularity, a lower inventory may be re-quired and it may be possible to reduce the bone plate set price. Also, custom plates may be assembled to meet specific patients' needs, on a case-by-case basis.

Further features and advantages will become apparent from the description of embodiments by means of the accompanying drawings.

BRIEF DESCRIPTION OF THE DRAWINGS

FIG. 19 shows a perspective view from the top of a first end piece of the bone plate of FIGS. 1 to 4.

FIG. 20 shows a cross-sectional view of the first end piece of FIG. 19.

FIG. 21 shows a perspective view from the top of a second end piece of the bone plate of FIGS. 1 to 4.

FIG. 22 shows a cross-sectional view of the second end piece of FIG. 21.

DETAILED DESCRIPTION OF PREFERRED EMBODIMENTS

Figure 1:
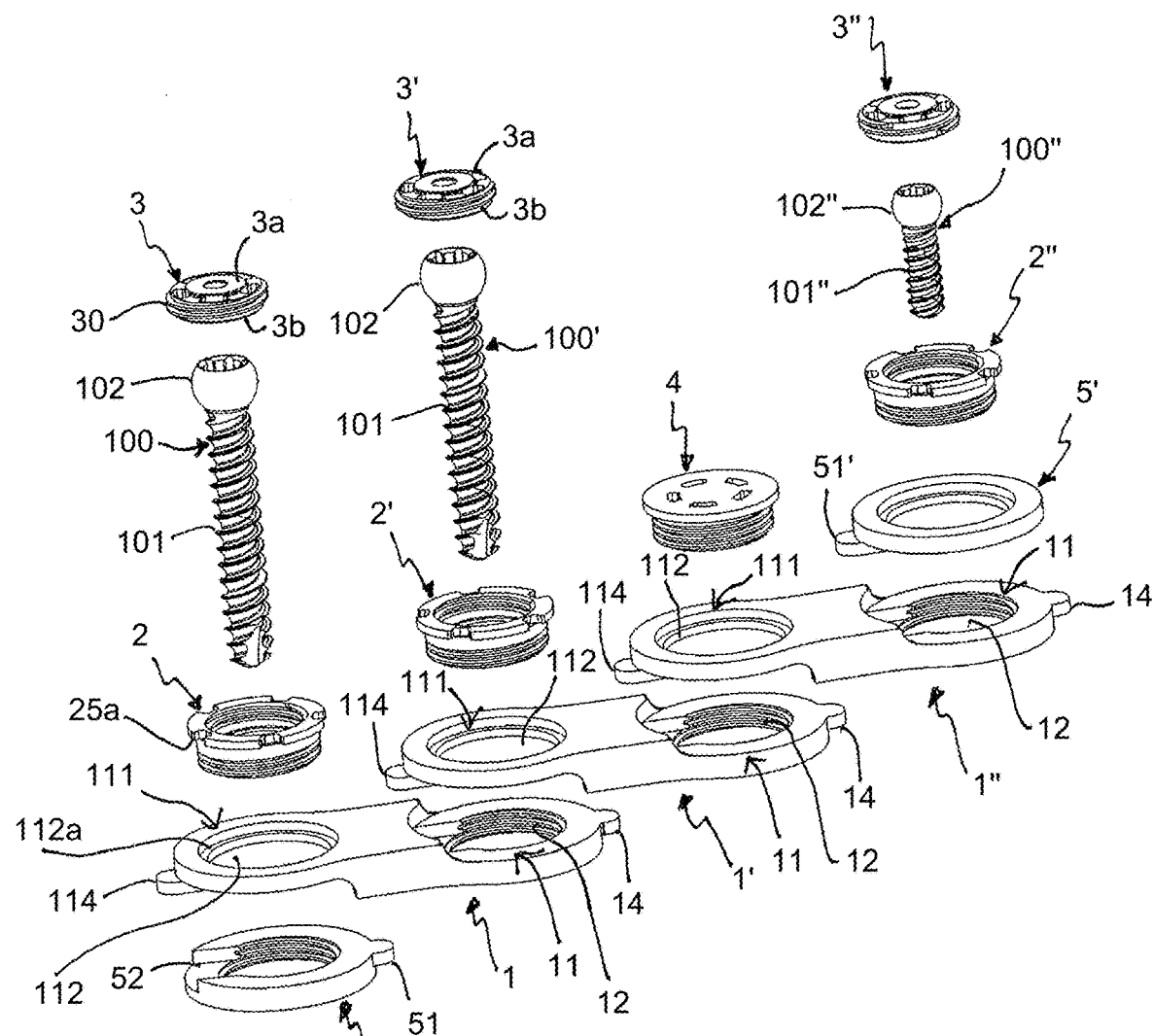
FIG. 1 shows a perspective exploded view of an embodiment of the modular bone plate.

As shown in FIGS. 1 to 4, the modular bone plate according to an embodiment includes at least a first plate member 1, a second plate member 1' and optionally a third plate member 1" or further plate members that are to be connected to each other. For connecting the plate members 1, 1', 1" connector members 2, 2', 2" are provided that are configured to receive at least a portion of a bone anchor 100, 100', 100" therein. The bone anchors may be secured, for example, against backing out once they are implanted into the bone via locking members 3, 3', 3" that are configured to be inserted into the connector members 2, 2', 2", respectively. One or more plug members 4 may be provided for connecting the plate members instead of using the connector members 2, 2', 2". Moreover, end pieces 5, 5' may optionally be provided that are configured to be connected to the plate members for forming an end of the bone plate.

In FIG. 1, two different types of bone anchors are shown. The bone anchors 100, 100' have a shank 101 with a first shank diameter and a head 102, 102' with a first maximum head diameter. The bone anchor 100" has a shank 101" with a second shank diameter smaller than the first shank diameter and a head 102" with a second head diameter smaller than the first head diameter. As depicted in the Figure, the heads 102, 102" have a spherically-shaped outer surface portion.

Figure 2:
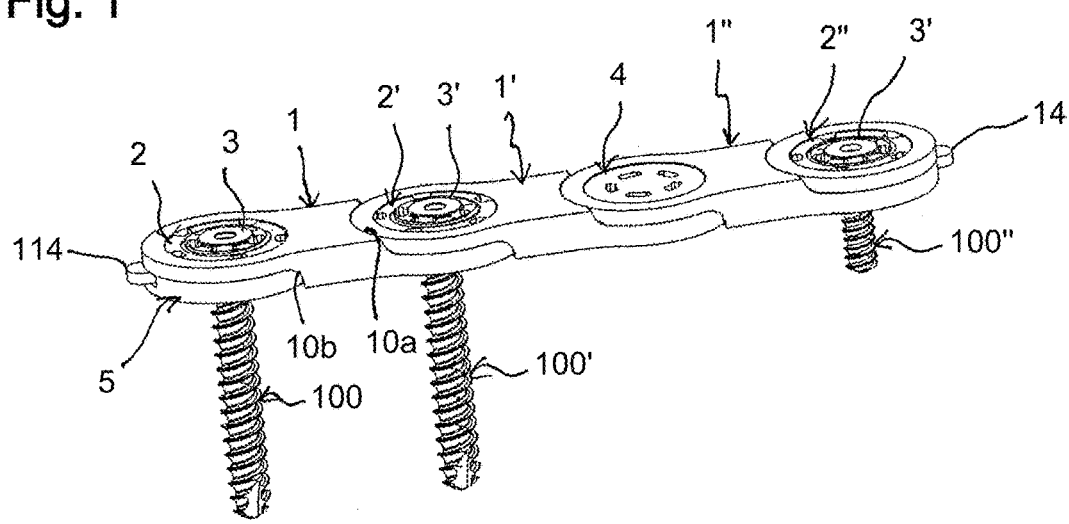
FIG. 2 shows a perspective view of the bone plate of FIG. 1 in an assembled state.
Figure 3:
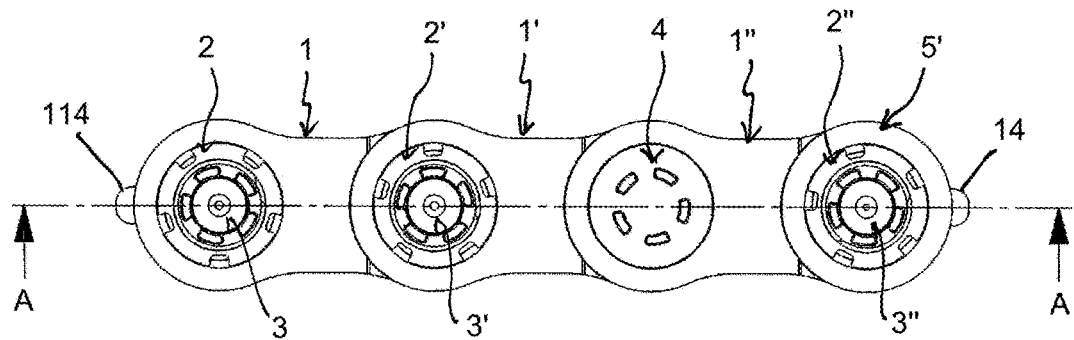
FIG. 3 shows a top view of the bone plate of FIG. 2.
Figure 4:
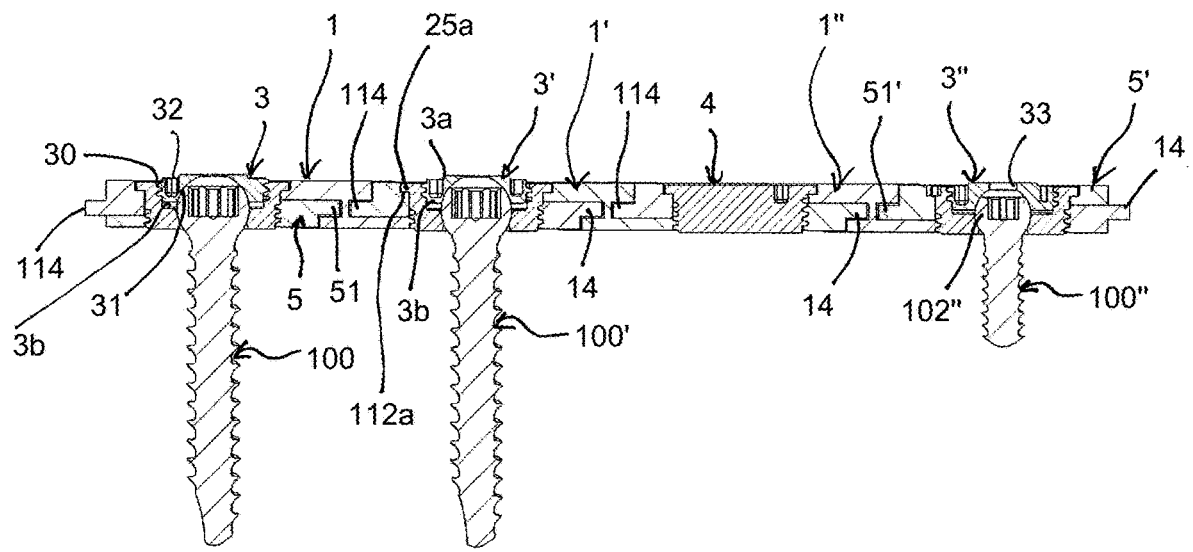
FIG. 4 shows a cross-sectional view of the bone plate of FIGS. 2 and 3 along line A-A in FIG. 3.
Figure 5:
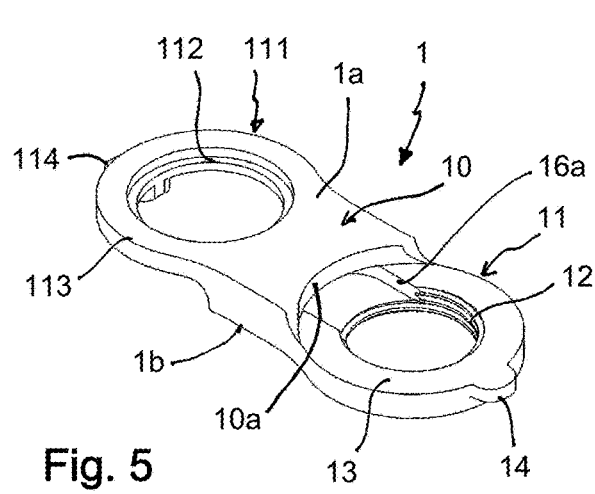
FIG. 5 shows a perspective view from the top of a plate member of the modular bone plate of FIGS. 1 to 4.
Figure 6:
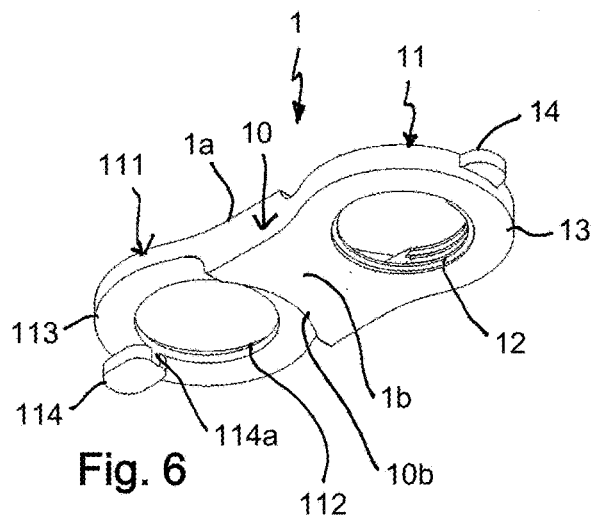
FIG. 6 shows a perspective view from the bottom of the plate member of FIG. 5.
Figure 7:
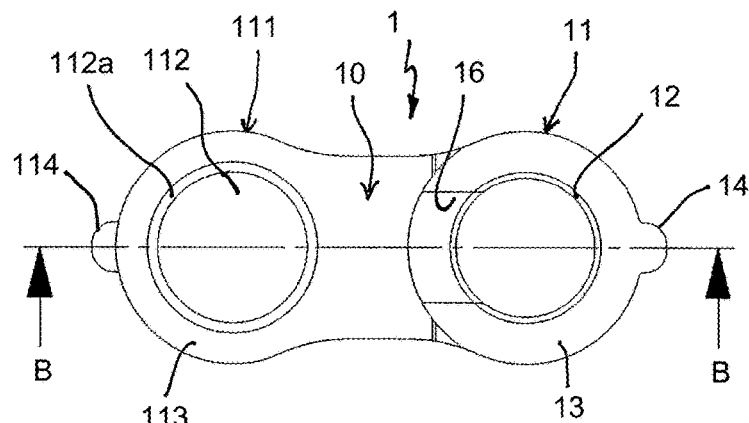
FIG. 7 shows a top view of the plate member of FIGS. 5 and 6.
Figure 8:
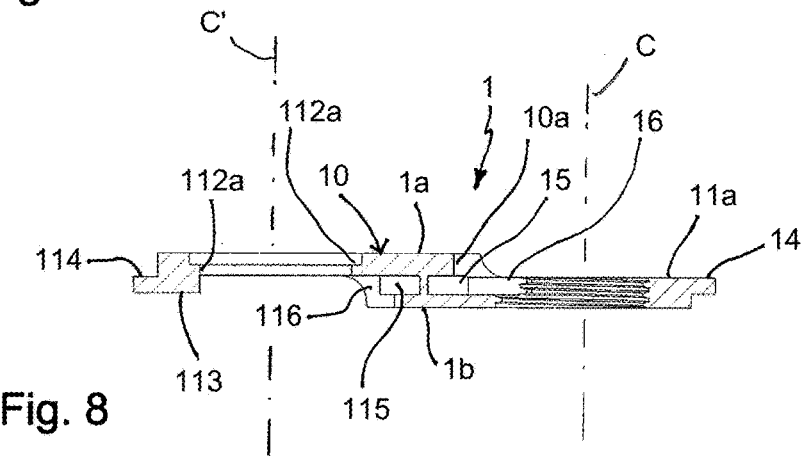
FIG. 8 shows a cross-sectional view of the plate member of FIGS. 5 to 7 along line B-B in FIG. 7.
Figure 9:
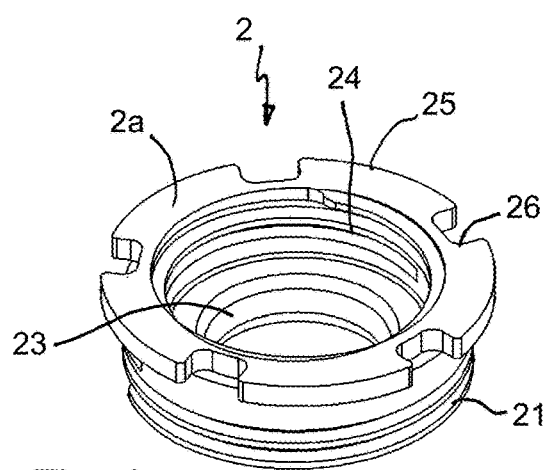
FIG. 9 shows a perspective view from the top of a first connector member of the bone plate according to FIGS. 1 to 4.
Figure 10:
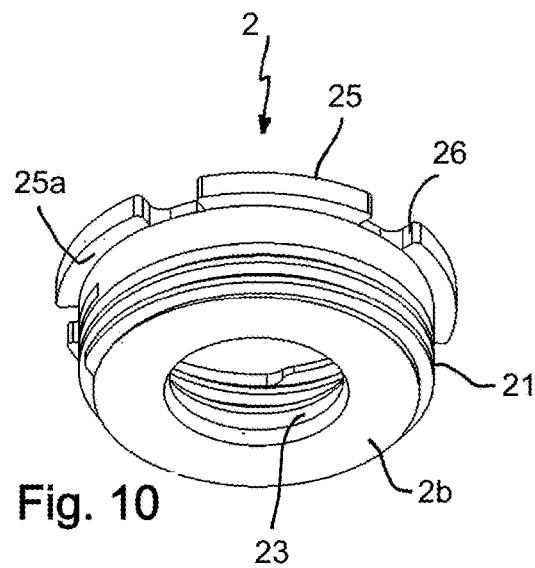
FIG. 10 shows a perspective view from the bottom of the connector member of FIG. 9.
Figure 11:
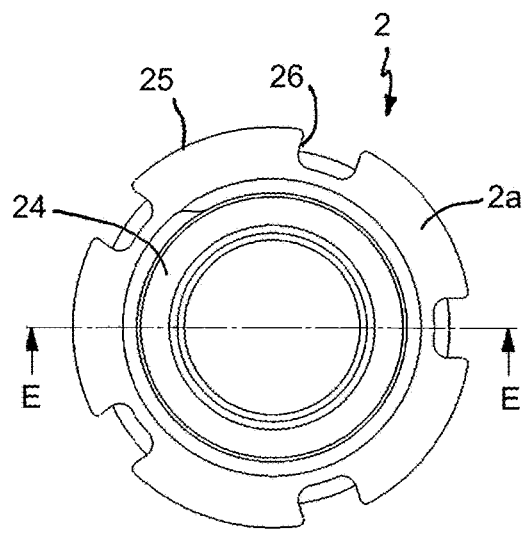
FIG. 11 shows a top view of the connector member of FIGS. 9 and 10.

As shown in FIGS. 2 to 4, the bone plate may be assembled from the plate members 1, 1', 1" connected by the connector members 2, 2', 2" and the plug members 4. Then the bone anchors 100, 100', 100" may be inserted into the connector members 2, 2', 2" and secured by the locking members 3, 3', 3".

Turning now in more detail to FIGS. 5 to 8, a plate member 1 will be described. The other plate members 1', 1" in this embodiment are identical to the plate member 1. The plate member 1 comprises a central plate portion 10 that has a top surface 1a and an opposite bottom surface 1b. As bottom surface 1b the surface is defined that faces the bone surface when the bone plate is to be attached to the bone. The plate member 1 therefore has a thickness in the plate portion 10 that corresponds to the distance of the top surface 1a from the bottom surface 1b. It shall be mentioned that while the plate portion 10 has a constant thickness in the embodiment shown, the plate portion 10 may also have a varying thickness, or one or both of the surfaces may be curved or other deviations from a constant thickness may be contemplated.

The plate member 1 further comprises a first connection portion 11 that extends laterally away from the plate portion 10 and that serves for connecting the plate member 1 to another plate member V. The connection portion 11 comprises a first hole 12 with a central axis C, the first hole being at least partially threaded for cooperating with an external thread of the connector member 2. Around the first hole, the connection portion 11 has a substantially circular outer contour forming an edge 13. As can be seen in particular in FIGS. 6 and 8, a lower surface of the first connection portion 11 is flush with the bottom surface 1b of the plate portion 10. A height of the first connection portion 11, however, is smaller than the height of the plate portion 10 so that an upper surface of the first connection portion 11 is below the top surface 1a of the plate portion 10. At an outer end of the first connection portion 11 opposite to the plate portion 10 a projection 14 is formed that constitutes an outermost free end of the plate member 1. The projection 14 extends in a plane perpendicular or at least substantially transverse to the center axis C of the first hole 12 and has a width in this plane that is smaller than a greatest width of the plate member in said plane. More specifically, the projection 14 is formed as a lug and has a substantially circular outer contour with the radius of the circle being considerably smaller that the radius of the first hole 12. In a circumferential direction, the projection 14 has a width that is less than a quarter circle of a circumference of the first hole 12. In a height direction, i.e. in a direction parallel to the center axis C of the first hole 12, the projection 14 extends from the upper surface of the first connection portion 11 to a distance from the upper surface.

Figure 25:
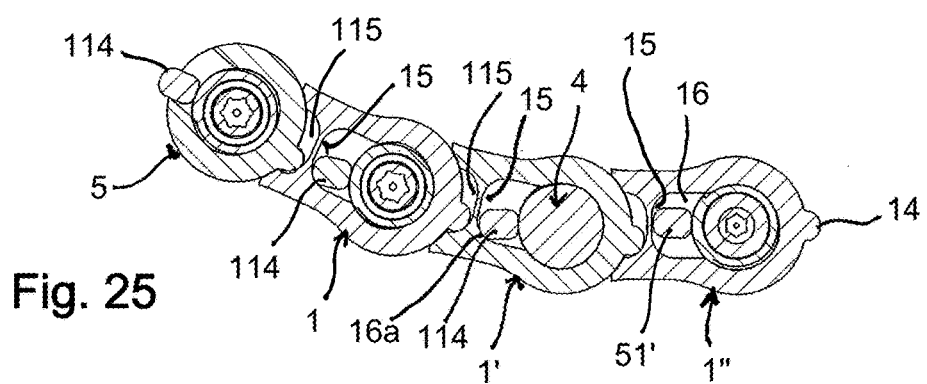
FIG. 25 shows a cross-sectional view of the bone plate of FIG. 24.
Figure 27:
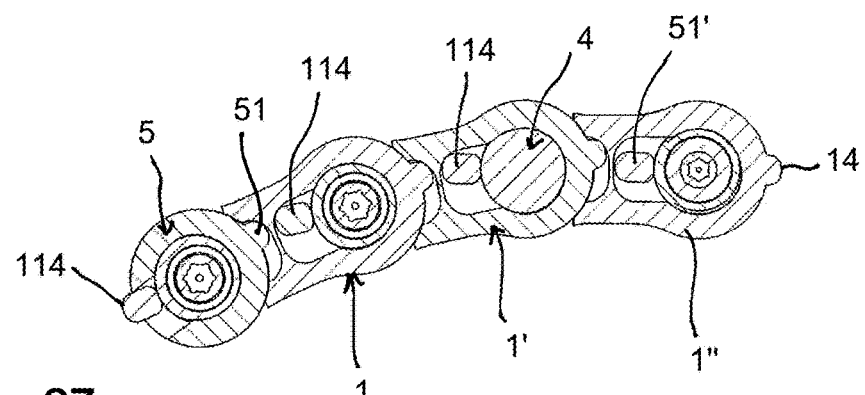
FIG. 27 shows a cross-sectional view of the bone plate of FIG. 26.

At a position opposite to the projection 14 in the plate portion 10 a groove 15 is provided that extends within the plate portion 10 at a distance from the edge 13 (see also FIGS. 25 and 27). The groove 15 forms the end portion of a recess 16 that is cut out in the top surface 11a of the first connection portion 11 and that extends substantially transverse to the center axis C of the first hole 12. A width of the recess and therefore also of the groove 15 in a direction perpendicular to the center axis C and perpendicular to a longitudinal axis of the recess 16 is greater than a width of the projection 14. The groove 15 and the recess 16 are at a height measured from the bottom surface 1b that corresponds to the height of the projection 14. Sidewalls 16a of the recess 16 form a stop for a projection provided at the other plate member as explained more in detail below.

In addition, the plate portion 10 comprises at the side facing towards the first connection portion 11 a recess 10a that forms a stop for a portion of another plate member when the plate members are to be assembled.

On the side opposite to the first connection portion, the plate member 1 comprises a second connection portion 111 with a second hole 112 having a center axis C' and an edge 113 with a substantially circular contour surrounding the second hole 112. The second hole 112 is thread-less. In the second hole 112 a circumferential shoulder 112a is provided at a distance from the upper surface that forms a stop for a connector member 2 as explained below.

An upper surface of the second connection portion 111 is flush with the top surface 1a of the plate portion 10 and a lower surface of the second connection portion 111 has a distance from the bottom surface 1b of the plate portion 10 in the height direction. At an outermost end of the second connection portion 111 a projection 114 is formed that constitutes an outermost end of the plate member 1. The projection 114 is located at the lower surface of the second connection portion 111 such that it has the same height as the projection 14 of the first connection portion 11. In a view from the bottom of the plate member 1 the projection 114 has a substantially rectangular shape with rounded edges. A thickness of the outermost portion of the projection 114 depicted in FIG. 6, the projection 114 is connected through a rib 114*a* with the edge 113 of the second connection portion 111. In the same manner as the projection 14, the projection 114 extends in a plane substantially transverse to the center axis (C') of the second hole (112) and has a width in said plane that is smaller than a greatest width of the plate member in said plane. The plate portion 10 comprises another recess 10*b* facing towards the second connection portion 111 that forms an abutment for the first connection portion 11 of another plate member.

Opposite to the projection 114 with respect to the second hole 112 a groove 115 is provided in the plate portion 10 that extends within the plate portion 10 at a distance from the edge 113 (see also FIGS. 25 and 27). The groove 115 forms an end portion of a recess 116 in the lower surface of the second connection portion 111, the middle axis of the recess being substantially perpendicular to the center axis of the second hole 112. By this design, the connection portions 11, 111 are similar, but inversely shaped in such a manner that the second connection portion 111 is configured to cooperate with a first connection portion 11 of another plate member 1' and the first connection portion 11 is configured to cooperate with a second connection portion 111 of another plate member 1".

It shall be noted that the plate portion 10 of the plate member 1 can have various shapes and lengths. Plate members having the same of a different shape can be combined to form a bone plate. The first and the second connection portions, however, have always the same shape for each plate member 1, 1', 1".

Turning now to FIGS. 9 to 12, the connector member 2 is a substantially cylindrical piece with a top surface 2*a* and an opposite bottom surface 2*b*. An external thread 21 is provided in at least a portion of the outer surface of the connector member 2, wherein the external thread 21 is configured to cooperate with the threaded first hole 12 of the plate member 1. In addition, the connector member 2 comprises a passage 22 that extends from the top surface 2*a* to the bottom surface 2*b* completely through the connector member 2. The passage 22 allows to pass a shank 101 of the bone anchor 10, 10', 10" therethrough. In the passage 22, at a distance from the bottom surface 2*b* a seat portion 23 for a head 102 of the bone anchor is formed. The seat portion 23 has a spherical segment-shape and is oriented such that the diameter increases towards the top surface 2*a*, so that the head 102 cannot pass through a lower opening of the connector member 2. Adjacent to the top surface 2*a* a substantially cylindrical recess 24 is provided that has at least in a portion thereof an internal thread 24*a* for screwing in the locking member 3. An inner diameter of the recess 24 may be greater than a greatest inner diameter of the seat portion 23, such that the locking member 3 can be inserted and placed over the head 102 of the bone anchor. At the top surface 2*a*, a circumferentially extending rim 25 is formed that extends outward beyond the external thread 21. The rim 25 may comprise recesses 26 that are open to the outside and serve for easy gripping and inserting of the connector member. A lower surface 25*a* of the rim 25 serves as an abutment or stop when inserting the connector member 2 into the holes 12, 112 of the connection portions 11, 111.

Figure 12:
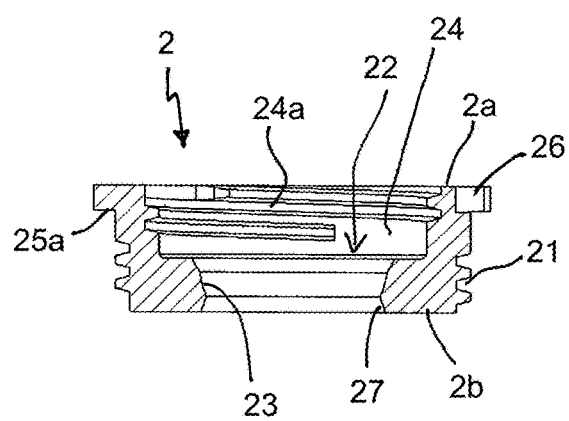
FIG. 12 shows a cross-sectional view of the connector member of FIGS. 9 to 11 along line E-E in FIG. 11

As further shown in FIG. 12, adjacent to the bottom surface 2*b*, a conically widening section 27 may be provided to allow the bone anchor 100 to pivot in the seat portion 23 when it is not yet screwed into the bone. A total axial length of the connector member may be such that the top surface 2*a* is in the assembled state flush with the top surface 1*a* of the plate member and the bottom surface 2*b* of the connector member 2 is flush with the bottom surface 1*b* of the plate member.

Figure 13:
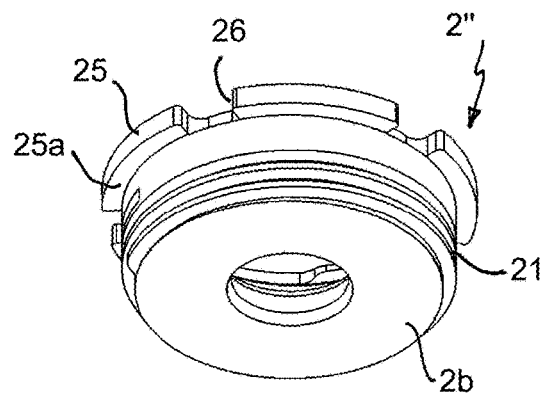
FIG. 13 shows a perspective view from the bottom of a second connector member.
Figure 14:
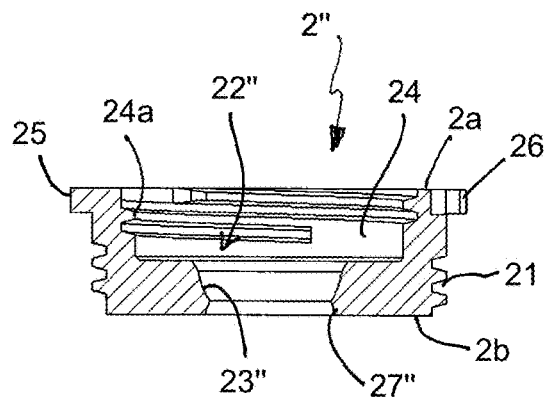
FIG. 14 shows a cross-sectional view of the second connector member of FIG. 13.
Figure 15:
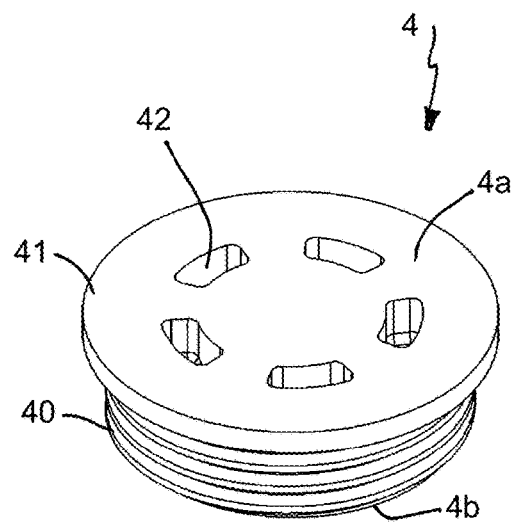
FIG. 15 shows a perspective view from the top of a plug member of the bone plate according to FIGS. 1 to 4.
Figure 16:
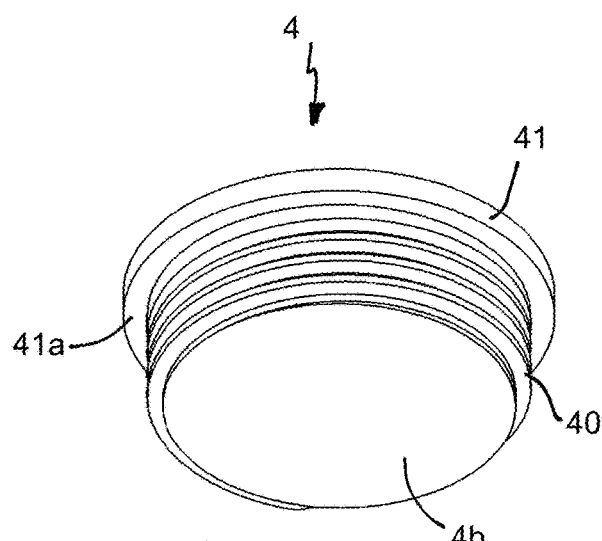
FIG. 16 shows a perspective view from the bottom of the plug member of FIG. 15.
Figure 17:
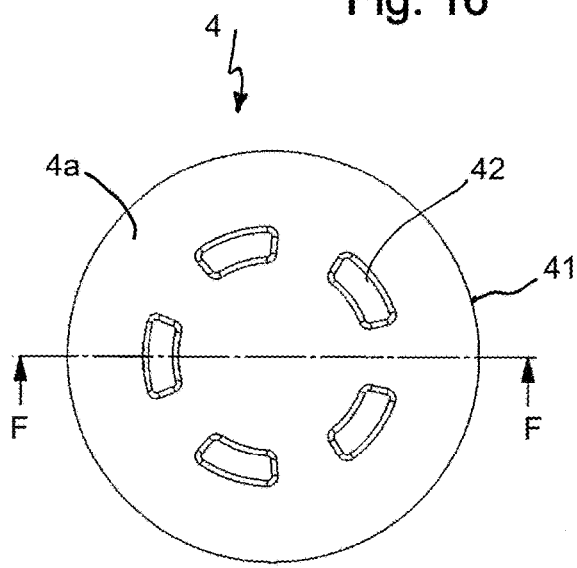
FIG. 17 shows a top view of the plug member of FIG. 15.
Figure 18:
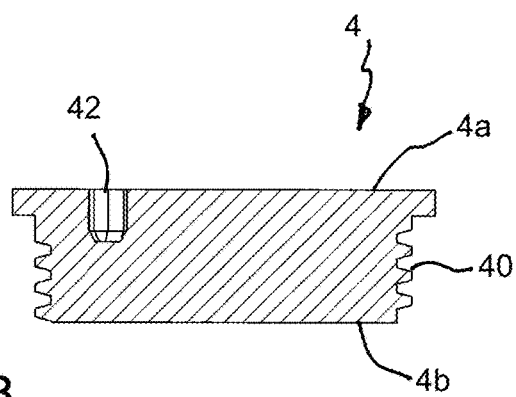
FIG. 18 shows a cross-sectional view of the plug member of FIGS. 15 to 17 along line F-F in FIG. 17.

Referring to FIGS. 13 and 14, a second connector member 2" is shown that is also depicted in FIGS. 1 to 4. The second connector member 2" differs from the first connector member as shown in FIGS. 9 to 12 only in the size of the passage 22'. More in detail, the minimum and maximum diameter of the spherical seat portion 23" and of the conically widening portion 27" are smaller compared to the maximum and minimum inner diameter of the seat portion 23 and of the conically widening portion 27 of the first connector member 2. All other portions and the sizes of the portions are identical to that of the first connector member 2. By means of this, the second connector member 2" is configured to accommodate a bone anchor 100" that differs with respect to the size of the head and of the shank. With such a design, the second and the first connector members can be used interchangeably and selectively.

As can be seen in FIGS. 15 to 18, the plug member 4 is formed as a substantially cylindrical part with a solid cylinder having a top surface 4*a* and an opposite bottom surface 4*b*. At an outer surface of the plug member an external thread 40 is formed and the plug member has such a size that it can be inserted into the first hole 12 and the second hole 112 when they overlap in the assembled state as shown in FIGS. 1 to 4. Thereby, the plug member engages with its external thread 40 the internal thread of the first hole 12 of the first connection portion 11. At the top surface 4*a*, the plug member 4 comprises an annular rim 41 that extends in a radial direction beyond the external thread 40. A lower surface 41*a* of the rim serves as an abutment or stop when the plug member 4 is inserted into the first hole 12 and the second hole 112. In addition, plurality of engagement portions for a driver in the form of circumferentially arranged recesses 42 are provided in the top surface 4*a* of the plug member 4. The recesses 42 may be located at a distance from the outer edge of the rim 41 and outside a center of the top surface 4*a*. In a top view, the recesses 42 may have an elongate, circular segment-shaped contour. It shall be noted that the engagement portions may also be shaped like the recesses 26 of the rim 25 of the connector member or may be realized as a polygon recess in the center of the plug member 4. A total height of the plug member may be such that the top surface 4*a* and the bottom surface 4*b* are flush with the top surface 1*a* and the bottom surface 1*b* of the plate member 1, respectively.

The locking member 3 will be explained more in detail referring to FIGS. 1 to 4. The locking member 3 is a substantially cylindrical part with a top surface 3*a* and a bottom surface 3*b* and with an external thread 30 that is configured to cooperate with the internal thread 24*a* of the connector member 2. Adjacent to the bottom surface 3*b* a recess 31 is provided that serves for accommodating a portion of the head of the bone anchor therein. The recess 31 may have a spherical segment-shape adapted to the shape of the head 102 of the bone anchor 100 so that the locking member 3 may contact the head and exert pressure onto the head when the locking member 3 is inserted into the connector member 2. In the top surface 3*a* a plurality of recesses 32 in the form of pockets may be provided that are arranged on a circular line around the center of the locking member 3 and at a distance from an outer edge of the locking member 3. The recesses 32 serve for engagement with a tool, such as a driver, used to insert and tighten the locking member 3. Moreover, in the top surface 3*a*, a central hole 33 may be provided. A height of the locking member 3 may be such that the top surface 3*a* is substantially flush with the top surface 1*a* of the plate portion 10 or projects only to a small extent above the top surface 1*a* of the plate portion 10.

Referring now to FIGS. 19 and 20, the first end piece 5 is a substantially ring-shaped piece with a top surface 5*a* and a bottom surface 5*b* and an internal thread 50. At one side, a projection 51 is provided that corresponds in size and shape to the projection 14 of the first connection portion. In other words, the projection 51 is formed as a lug that extends from the upper surface 5*a* outward and extends in a height direction to a distance from the lower surface 5*b*. Opposite to the projection 51 a recess or cutout 52 is provided in the top surface 5*a* of the first end piece 5 that corresponds in shape and size to the recess 16 of the first connection portion 11 of the plate member 1. In other words, the recess 52 has a width that is greater than the width of the connection portion 51 and extends perpendicular to a center axis of the ring. A depth of the recess 52 also substantially corresponds to the thickness of the projection 51. The first end piece 5 is configured to cooperate with the second connection portion 111 of the plate member 1.

Referring to FIGS. 21 and 22, the second end piece 5' is also a ring-shaped part that has a top surface 5*a* and a bottom surface 5*b*. At one side, a projection 51' extends outward from below the lower surface 5*b*. The projection 51' has an elongate substantially rectangular shape with rounded edges that is similar to that of the projection 114 of the plate member 1. More in detail, a thickness of the projection 51' is such that the projection 51' can be inserted into the groove 15 of the first connection portion 11 of the plate member 1. At an inner wall of the ring of the second end piece 5' an annular step or abutment 52*a* is formed serving as a stop for the connector member. The second end piece 5' is configured to cooperate with the first connection portion 11.

The plate members, the connector members, the plug members and the locking members as well as the bone anchors may each be made of a bio-compatible material, for example of tita-nium or stainless steel, of a bio-compatible alloy, such as NiTi-alloys, for example Nitinol, of magnesium or magnesium alloys, or from a bio-compatible plastic material, such as, for example, polyether ether ketone (PEEK) or poly-L-lactide acid (PLLA). Moreover, the parts can be made of the same or of different materials.

The assembly of the modular bone plate will now be described with reference to FIGS. 1 to 4. To connect the plate members 1, 1', 1" the plate members are oriented such that the first connection portion 11 of a first plate member 1 overlaps with the second connection portion 111 of a second plate member 1', or in the case of three plate members, the first connection portion 11 of the second plate member 1' overlaps with the second connection portion 111 of the third plate member 1". Thereby, the projections 114 of the second connection portion enter through the recess 16 into the groove 15 of the first connection portion 11. Simultaneously, the projection 14 of the first connection portion enters through the recess 116 into the groove 115 of the second connection portion 111. When the projections are fully introduced into the grooves, the first hole 12 and the second hole 112 are concentric. The bottom surfaces 1*b* and the top surfaces 1*a* of the plate portions 10 and the connection portions 11, 111 are substantially flush, as can be seen in particular in FIGS. 2 and 4. The outermost portions of the edges 13, 113 abut against the recesses 10*a*, 10*b* of the plate portion 10.

Thereafter, the connector members are screwed into the threaded first hole 12 of the first connection portion until the lower surface 25*a* abuts against the stepped portion 112*a* of the second connection portion 111. Thereby, the plate members are firmly connected. The abutment of the connector member against the stepped portion 112*a* results in a compressing force which the connector member 2 exerts onto the second connection portion 111 towards the first connection portion 11 of a neighbouring plate member. By means of this, the strength of the connection is enhanced. In addition, the design of the projection and groove results in an enhanced stiffness against bending forces that may act onto the bone plate.

Figure 23:
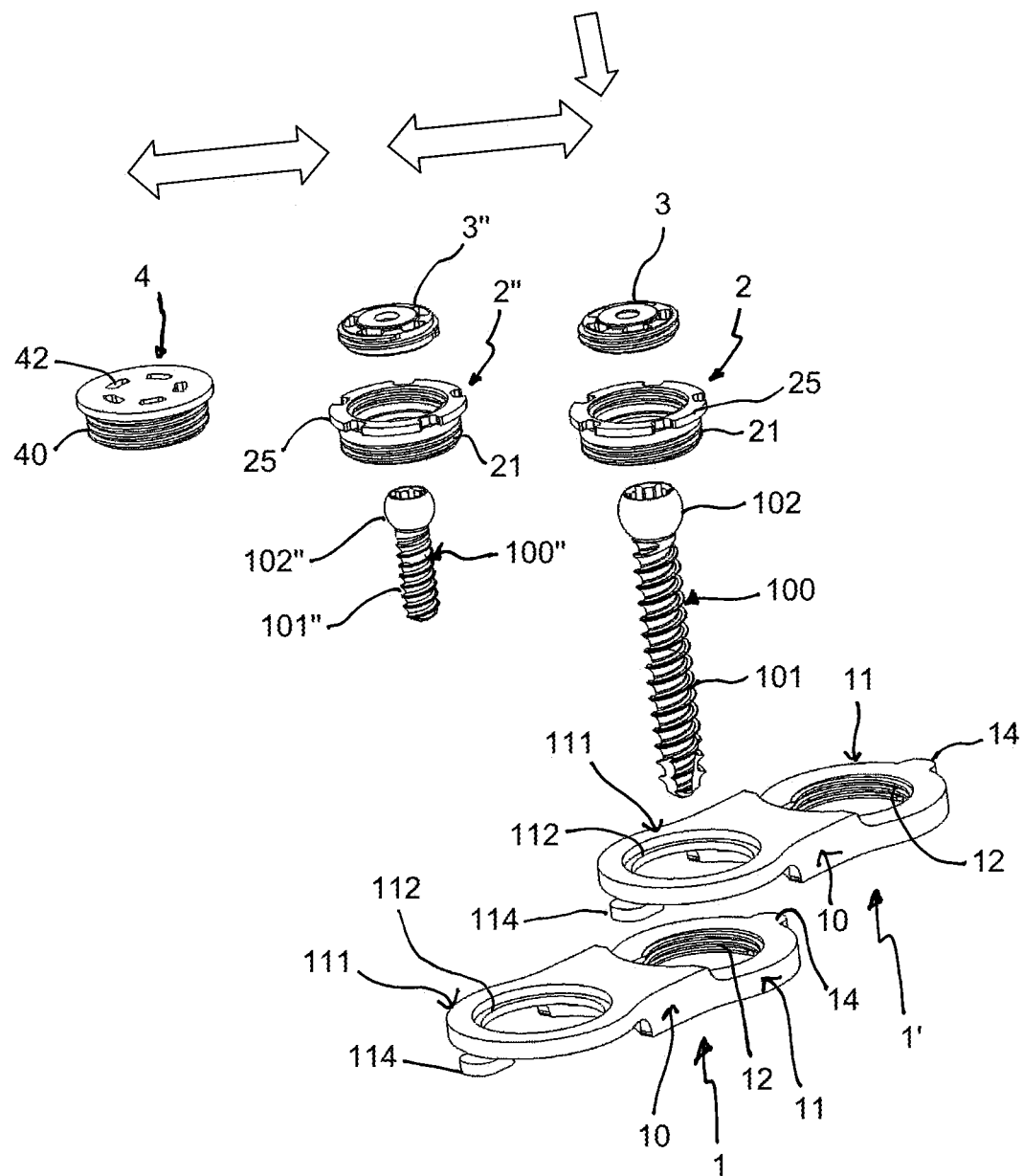
FIG. 23 shows a perspective exploded view of the bone plate of FIGS. 1 to 4 with different connector members and different bone anchors and with a plug member.

Turning now to FIG. 23, the versatility of the modular bone plate is shown. A first connector member 2 can be used with a first bone anchor 100 having a first shank diameter and a first head diameter. Depending on the clinical application, instead of the first connector member 2, a second connector member 2" can be used together with a second bone anchor 102" having a smaller shank diameter and a smaller head diameter. Further, if a bone anchor is not necessary at a particular position of the bone plate, a plug member 4 can be used instead of the connector members to close the holes.

Once the bone plate has been assembled from the plate members and the connector members, the modular bone plate can be placed onto the bone without the members falling apart. When the modular bone plate has been placed onto the bone, the bone anchors 100, 100', 100" can be inserted so that the spherical head of each bone anchor is seated in the seat portion 23, 23' of a corresponding connector member 2, 2', 2". Each bone anchor may assume various angular posi-tions with respect to the bone plate, because the head is accommodated in the seat in the manner of a ball and socket joint.

Once one or several bone anchors have been placed, the locking member 3 can be screwed into the connector member 2 to secure the bone anchor 100 in the plate and prevent backing out of the bone anchor. The locking member 3 may be used to press onto the head 102 of the bone anchor or may be used to just provide a closure for the passage 22 in the connector member 2 without contacting the head.

Referring again to FIGS. 1 to 4, the end pieces 5, 5' may be used to form an end area of the bone plate that has the same or substantially the same thickness as other areas of the bone plate. The first end piece 5 that resembles the first connection portion is connected with its projection 51 to the groove 115 of the second connection portion 111 of a plate member 1 so that the holes of the end piece 5 and of the second connection portion 111 overlap. The second end piece 5' is connected with its projection 51' to the groove 15 of the first connection portion 11, so that the holes of the end piece 5' and of the first connection portion 11 overlap.

Figure 24:
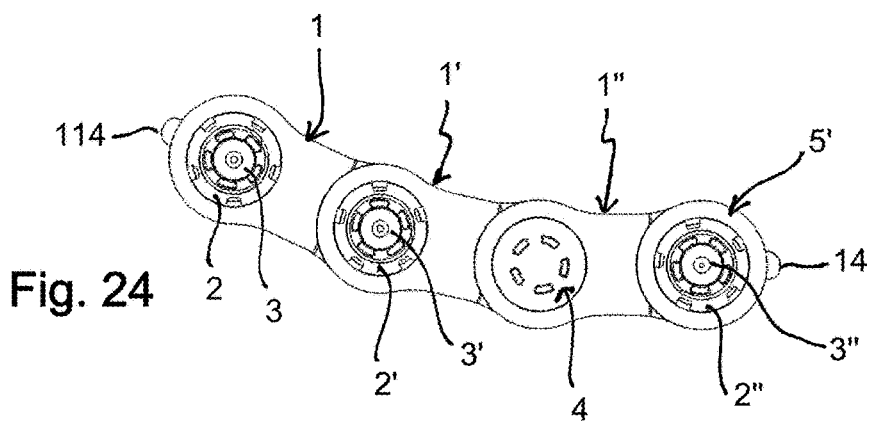
FIG. 24 shows a top view of a bone plate assembled from a plurality of plate members in a first angled configuration.

In FIGS. 24 and 25 the modular bone plate of FIG. 1 is shown in a curved configuration. To achieve this, the plate members 1, 1' are rotated in one direction one relative to the other until the projections 114 of the second connection portion 111 abut against the wall of the groove 15 of the first connection portion 11 at the transition to the recess 16. Simultaneously, the projections 14 of the first connection portion abut against the wall of the groove 115 of the second connection portion 111 at the transition to the recess 116. Also, the first end piece 5 is rotated with respect to the first plate member 1 so that its projection 51 abuts against the wall of the groove 115 of the second connection portion 111. The second end piece 5' may be or may not be rotated, depending on the requirements for the bone plate. The maximum curvature of the bone plate is defined by the maximum angle that can be achieved when rotating the plate members relative to each other which is limited by the above described abutment.

Figure 26:
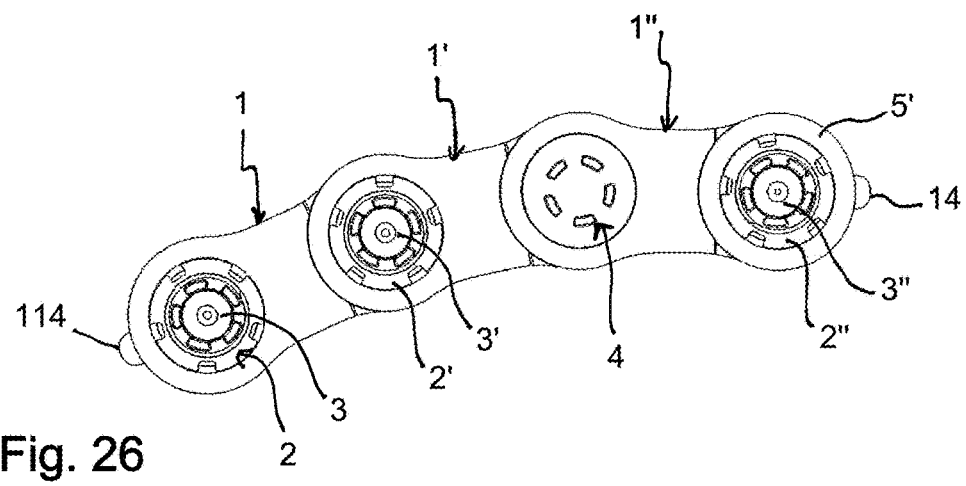
FIG. 26 shows a bone plate assembled from a plurality of plate members in a second angled configuration.

In FIGS. 26 and 27 the modular bone plate of FIG. 1 is shown in a curved configuration with a curvature opposite to the curvature of the modular bone plate shown in FIGS. 24 and 25. To achieve this, the plate members are rotated one relative to the other in the opposite direction compared to that shown in FIGS. 24 and 25 and the projections abut at the opposite side of the wall of the grooves at the transition to the recess, respectively.

It shall be noted that any angled configuration between the two maximum angles shown in FIGS. 24 and 25 at the one hand and FIGS. 26 and 27 at the other hand can be arranged. It is also possible to have various curvatures along the whole length of the bone plate.

Figure 28:
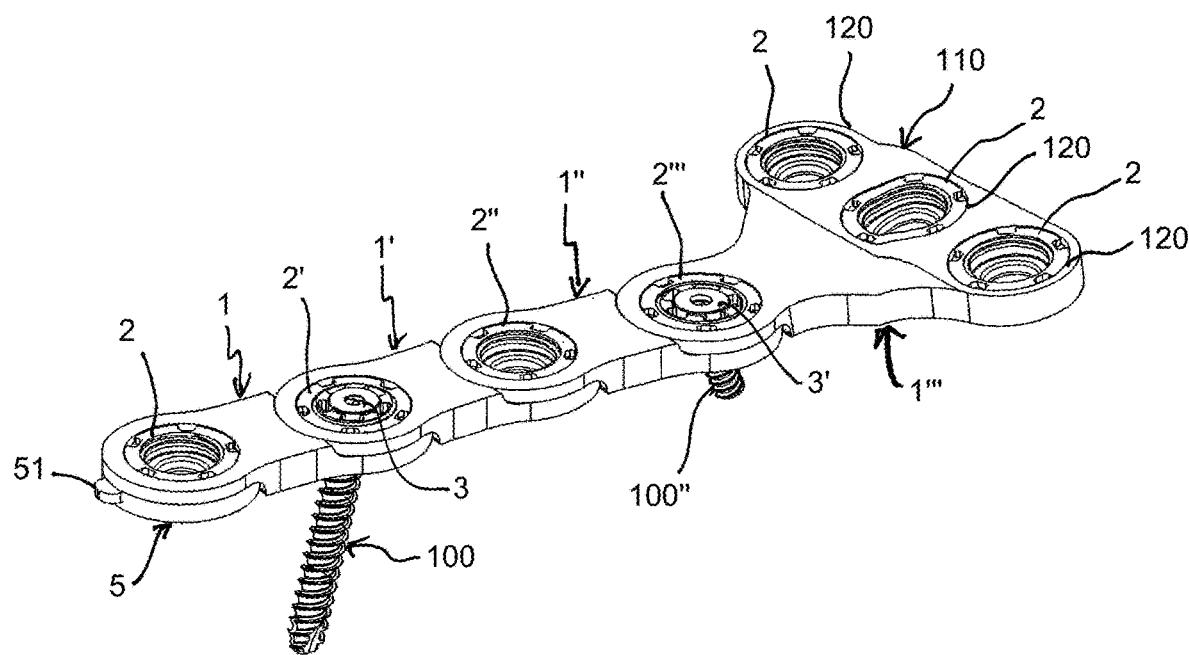
FIG. 28 shows a perspective view of a bone plate according to a modified embodiment.

FIG. 28 shows a modified embodiment of the modular bone plate with a further type of a plate member 1'''' that is substantially T-shaped. The plate member 1''' comprises a second connection portion 111 at one end and an end portion 110 that extends substantially transverse to the second connection portion 111. The end portion 110 may have one or more holes 120 with connector members 2 to be placed therein.

It should be clear that the plate members can be designed in many configurations and are not limited to the specific embodiments shown above. For example, the contour of the plate members may vary, the plate members can be angled in a plane perpendicular to the axis of the holes or also in a plane containing the axis of the holes. The holes may have an axis that is inclined with respect to the top and/or the bottom surface of the plate portion.

The seat portion in the connector member may be shaped other than spherical, for example con-ical. The seat may also have a shape that prevents an angled insertion of the bone anchor or permits angled insertion only in a specific direction or specific plane. In this case the bone anchor may also have a head with another shape.

The locking member may be omitted or designed in another shape. The end pieces may be omitted.

What is claimed is:

1. A modular bone plate system, including:
   a first plate member including a first connection portion comprising a first hole and an end portion extending substantially transverse to the first connection portion, the end portion provided with at least two end portion holes; and
   a second plate member including a second connection portion comprising a second hole;
   wherein the first plate member is connectable to the second plate member when the first plate member and the second plate member are arranged such that the first hole and the second hole overlap;
   a first connector member insertable into the first hole and the second hole when the first hole and the second hole overlap such as to connect the first plate member and the second plate member; and
   a first bone anchor, the first bone anchor being a polyaxial bone anchor having a partially spherical head and a shank for anchoring in bone,
   wherein the first connector member comprises a passage, the passage having a seat that is configured to accommodate the head of the bone anchor and permits the first bone anchor to seat at the first connector member at any one of multiple angles, and wherein the passage has a size for guiding through the shank of the bone anchor.

2. The modular bone plate system of claim 1, wherein the end portion of the second plate member includes at least three holes.

3. The modular bone plate system of claim 2, wherein the end portion of the second plate member includes four holes.

4. The modular bone plate system of claim 1, wherein the first connection portion and the end portion are angled out of plane from each other.

5. The modular bone plate system of claim 1, wherein the seat comprises a spherical section upon which the partially spherical head seats.

6. The modular bone plate system of claim 1, wherein the second hole comprises a threaded section and wherein the first connector member comprises an outer threaded surface portion that is configured to cooperate with the threaded portion of the second hole.

7. The modular bone plate system of claim 6, wherein the first hole is unthreaded.

8. The modular bone plate system of claim 1, wherein the first and second plate members have different shapes.

9. The modular bone plate system of claim 1, further comprising:
   a third plate member; and
   a second connector member, wherein
   the second plate member includes a third hole, and
   the third plate member includes a fourth hole,
   wherein the third plate member is connectable to the second plate member when the third plate member and the second plate member are arranged such that the fourth hole and the third hole overlap, and the second connector member is inserted through the overlapping third and fourth holes,
   the second connector member including a passage that is sized for guiding through the shank of a second bone anchor.

10. The modular bone plate system of claim 9, wherein the second connector member has a same configuration as the first connector member.

11. The modular bone plate system of claim 9, further comprising:
    a fourth plate member; and
    a third connector member, wherein
    the third plate member includes a fifth hole, and
    the fourth plate member includes a sixth hole,
    wherein the fourth plate member is connectable to the third plate member when the fourth plate member and the third plate member are arranged such that the sixth hole and the fifth hole overlap, and the third connector member is inserted through the overlapping sixth and fifth holes,
    the third connector member having a same configuration as the first connector member.

12. The modular bone plate system of claim 11, wherein the passages of each of the first connector member, second connector member, and third connector member is the same size.

13. The modular bone plate system of claim 1, wherein the end portion of the first plate member is as thick as first plate member and the second plate member together where the first hole and the second hole overlap.

14. The modular bone plate system of claim 1, wherein:
    the first plate member defines a first longitudinal axis, a planar first lower surface surrounding the first hole, and a recess partially defined by sidewalls, and the second plate member defines a second longitudinal axis, a planar second upper surface surrounding the second hole and flushly in contact with the first lower surface, the second plate member having a projection extending coaxially with the second longitudinal axis, the projection extending within the recess, wherein the recess prevents release of the projection at a side of the recess when the projection is received in the recess and the first and second plates are rotated relative to each other.

15. A modular bone plate system, comprising:

a first plate member including a first connection portion comprising a first hole and an end portion extending substantially transverse to the first connection portion, the end portion provided with at least two end portion holes; and a second plate member including a second connection portion comprising a second hole;

wherein the first plate member is connectable to the second plate member when the first plate member and the second plate member are arranged such that the first hole and the second hole overlap;

a first connector member insertable into the first hole and the second hole when the first hole and the second hole overlap such as to connect the first plate member and the second plate member; and a first bone anchor having a head and a shank for anchoring in bone, wherein the first connector member comprises a passage that is configured to accommodate the head of the bone anchor and wherein the passage has a size for guiding through the shank of the bone anchor, wherein the at least two end portion holes in the end portion of the first plate member are provided with respective connector members having a same configuration as the first connector member.

* * * * *